United States Patent [19]

Ashida et al.

[11] Patent Number: 4,970,152
[45] Date of Patent: Nov. 13, 1990

[54] REAGENTS FOR DETERMINING PEPTIDOGLYCAN AND β-1,3-GLUCAN

[75] Inventors: Masaaki Ashida, Sapporo; Masakazu Tsuchiya, Itami; Yoshitsugu Sakata, Otsu; Shuji Matsuura, Kawanishi, all of Japan

[73] Assignee: Wako Pure Chemical Industries, Ltd., Osaka, Japan

[21] Appl. No.: 127,315

[22] Filed: Dec. 2, 1987

[30] Foreign Application Priority Data

Dec. 3, 1986 [JP] Japan .................................. 61-288244
Dec. 3, 1986 [JP] Japan .................................. 61-288245

[51] Int. Cl.$^5$ .......................... C12Q 1/44; C12Q 1/00; C12Q 1/37; C12Q 1/26
[52] U.S. Cl. ........................................ 435/19; 435/23; 435/25; 435/4; 435/815; 435/201; 435/206; 435/207; 435/208; 530/350; 530/380; 530/413; 530/417; 530/858
[58] Field of Search .................... 435/4, 19, 23, 25, 29, 435/34, 911, 201, 206, 207, 208, 209, 210, 211, 815; 530/350, 380, 413, 417, 858

[56] References Cited

PUBLICATIONS

Ashida, M., Insect Biochem., vol. 11, pp. 57–65, (1981).
Ashida, M., et al., Biochem. Biophys. Res. Comm., vol. 113, No. 2, pp. 562–568, (1983).
Yoshida, H., et al., Biochem. Biophys. Res. Comm., pp. 1177–1184, (1986).

*Primary Examiner*—Esther L. Kepplinger
*Assistant Examiner*—Toni R. Scheiner
*Attorney, Agent, or Firm*—Armstrong, Nikaido, Marmelstein, Kubovcik & Murray

[57] ABSTRACT

A reagent comprising a fraction obtained from plasma of an insect such as silkworm larvae and capable of reacting specifically with β-1,3-glucan or peptidoglycan can be used for determining β-1,3-glucan or peptidoglycan.

12 Claims, 4 Drawing Sheets

REAGENTS FOR DETERMINING PEPTIDOGLYCAN AND β-1,3-GLUCAN

BACKGROUND OF THE INVENTION

This invention relates to reagents for determining β-1,3-glucan or peptidoglycan and a method for determining β-1,3-glucan or peptidoglycan using the same.

β-1,3-Glucan (hereinafter referred to as "β-G") is present in nature as cell wall components of true fungi such as yeast and molds and as major polysaccharide components in fruit bodies of many basidiomycota. It is well known that β-G is positive in the so-called Limulus test which is a method for detecting endotoxin using a reagent purified from horseshoe crab hemocyte lysate. By applying this property of β-G, a method is proposed for determining β-G specifically with no influence of endotoxin, in which a reagent purified from horseshoe crab hemocyte lysate is used [Rinsho Byori (Clinical Pathology) 33, 639–644, 1985]. However such a method has not practically been used yet, because of a trouble such as a stability of the reagent. Further, there is proposed a method for detecting endotoxins or β-G by using a reagent obtained by purifying a blood cell lysate from a crustacean or an insect [PCT, International Publication No. WO 83/02123]. But the reagent used for this process has a property to react with both the endotoxins and β-G. Therefore, in order to use this reagent for determining specifically β-G, it is necessary to add anti-endotoxin factors purified from crayfish blood cells.

On the other hand, peptidoglycan (hereinafter referred to as "PG") is a kind of glycopeptide polymer constituting cell walls of bacteria and is contained more in cell walls of Gram-positive bacteria than in cell walls of Gram-negative bacteria. In general, PG is characterized by containing N-acetyl- or N-glycolylmuramic acid and D-amino acid. It has been known that PG has many biological activities such as having an attack of fever, lowering of functions of the liver and the kidney, enhancing the action of endotoxin activity, increasing effect of immune function (adjuvant activity) and the like. Thus, studies of PG have been made vividly in the fields of medical science, pharmacology, microbiology, etc., but a specific determination method has not been found.

Some of the present inventors previously found that a body fluid obtained from silkworm does not react with endotoxin but reacts with PG or β-G so as to activate at least three kinds of enzymes, i.e. an esterase hydrolyzing N-α-benzoyl-L-arginine ethyl ester (BAEEase), pro-phenoloxidase activating enzyme (PPAE), and phenoloxidase (PO) [Insect Biochem, vol 16, No. 3, pp. 539–545, 1986]. But since there was a problem in specificity, this was not applied to the determination of β-G or PG.

As mentioned above, since the determination methods are not established, effects of β-G or PG on human bodies are not fully known yet. But recently, there is a doubt that β-G is one cause for bringing about a shock at the time of using hemodicalysis film of cellulose derivatives, or there is a suggestion that β-G is present in a body fluid of a patient suffered from mycotic infection. Therefore, the determination of β-G or PG becomes more and more important in the fields of medical sciences, such as pharmacology and microbiology.

SUMMARY OF THE INVENTION

The present inventors have succeeded in removing a component, which specifically reacts with β-G or PG, from an insect plasma, and found that it is possible to determine β-G or PG by reacting the resultant plasma fractions with a sample to be tested containing β-G or PG and measuring expressed enzymatic activities of BAEEase, PPAE, PO, etc., or measuring the time required for these enzymatic activities to be expressed. Thus, the present invention has been accomplished.

This invention provides a reagent for determining β-1,3-glucan. The reagent comprises a fraction obtained from plasma of an insect and capable of reacting specifically with β-1,3-glucan.

This invention also provides a process for determining β-1,3-glucan which comprises reacting a sample with a reagent comprising a fraction obtained from plasma of an insect and capable of reacting specifically with β-1,3-glucan, and measuring enzymatic activity generated.

This invention further provides a process for determining β-1,3-glucan which comprises reacting a sample with a reagent comprising a fraction obtained from plasma of an insect and capable of reacting specifically with β-1,3-glucan, and measuring a time required for an enzymatic activity to be expressed.

This invention still further provides a reagent for determining peptidoglycan. The reagent comprises a fraction obtained from plasma of an insect and capable of reacting specifically with peptidoglycan.

This invention further provides a process for determining peptidoglycan which comprises reacting a sample with a reagent comprising a fraction obtained from plasma of an insect and capable of reacting specifically with peptidoglycan, and measuring the enzymatic activity generated.

This invention also provides a process for determining peptidoglycan which comprises reacting a sample with a reagent comprising a fraction obtained from plasma of an insect and capable of reacting specifically with peptidoglycan, and measuring a time required for an enzymatic activity to be expressed.

This invention still further provides a process for collecting a body fluid from an insect which comprises adding an insect body fluid to an isotonic solution for the insect to be used which contains a substance irreversibly inhibiting serine protease, and removing an excess amount of the inhibiting substance.

This invention still further provides a process for collecting a body fluid from an insect which comprises; injecting an isotonic solution for the insect to be used which contains a substance irreversibly inhibiting serin protease to the insect, cutting a part of the body, collecting a body fluid leaking out and removing an excess amount of the inhibiting substance.

DESCRIPTION OF THE PREFERRED EMBODIMENTS

As the insects which can give body fluids usable in this invention, there is no limitation thereto, but larger ones with known rearing methods therefor are preferable. Examples of such insects are *Manduca serta, Gelleria melonella, Hyalphoma ceropia, Bombyx mori* (silkmoth), etc., belonging to Lepidoptera order; Sarcophaga peregrina, musca, etc., belonging to Diptera order; Locusta, migratoria Teleogryllus, etc., belonging to Orthoptera order; Cerambyx belonging to Coleoptera order, etc.

As the body fluid, hemolymph which is obtained from a body cavity is most easily obtained and thus usually used.

The body fluid of insects can be collected, for example, by a method disclosed by M. Ashida [Insect Biochem., 11, 57–65 (1981)]. That is, insects, for example, silkworm larvae, are anesthetized on ice, and physiological saline containing sugar including as impurities cane sugar factor (polymeric substances included in a sugar cane and comprising glucose, amino acids, etc.), or containing cane sugar factor itself is injected into haemocoel (body cavity) of the silkworm larvae. Then the larvae body was tied with a fine thread so as to prevent leakage of the injected saline. After allowed to stand at room temperature for about 20 minutes, a leg was cut and the body fluid is collected. When the collected fluid is centrifuged to remove blood cells, followed by dialysis, an insect plasma can be obtained.

Alternatively, the body fluid of insects can be collected by a process newly devised by some of the present inventors. That is, to a solution isotonic to an insect body fluid to be collected and containing serine protease (hereinafter referred to as "SP") inhibitor (hereinafter referred to as "SPI") which is a substance irreversibly inhibiting SP, an insect body fluid is added and then excess SPI is removed. The insect body fluid without free SPI holds reactivity with $\beta$-G or PG.

Further, the body fluid of insects can also be collected by a process comprising injecting an isotonic solution for the insect to be used which contains a substance irreversibly inhibiting serine protease to the insect, cutting a part of the body, collecting a body fluid leaking out and removing an excess amount of the inhibiting substance. The insect body fluid without free SPI holds reactivity with $\beta$-G or PG.

As the SPI, there is no particular limitation thereto so long as it can irreversibly inhibit SP and it can be separated from the fraction of an insect body fluid which react with $\beta$-G or PG. Among the SPIs, preferable ones from the viewpoint of handling are those having relatively small molecular weights, e.g., 2000 or less, and being able to be removed by dialysis. Preferable examples of the SPI are (p-amizinophenyl)-methanesulfonyl fluoride (p-APMSF), phenylmethanesulfonyl fluoride (PMSF), diisopropylfluorophosphoric acid (DFP), p-nitrophenyl-p'-guanidinobenzoic acid (NPGB), dihydroxychloromethylcoumalin, etc.

It is sufficient to add to the above-mentioned isotonic solution the SPI in an amount at least necessary to inactivate SP which is to be activated during the collection of body fluid. Preferable amount of SPI in the isotonic solution is 0.1 to 10 mM, more preferably 0.5 to 5 mM.

This method can be carried out, for example, as follows:

To a solution containing SPI and isotonic to an insect body fluid to be collected, a body fluid leaked out of an injured portion of an insect is directly dropped. Alternatively, after injecting a solution containing SPI and isotonic to an insect body fluid to be collect into an insect, a body fluid leaked out of an injured portion of the insect is collected. Then, the collected fluid is centrifuged to remove blood cells, and the like. Further, excess SPI present in the resulting body fluid-containing solution is removed by one or more most suitable methods generally used in the field of biochemistry for separation and purification depending on the nature of SPI used, e.g. a dialysis method, a gel filtration method, an ion exchange method, high performance liquid chromatography, etc. As a result, the desired solution containing insect plasma can be obtained. Further, the SPI removal operation can be conducted after subjecting the centrifuged solution to concentration and purification to some extent by a conventional method such as fractionation with ammonium sulfate, or the like.

The thus obtained plasma contains substance(s) which does not react with endotoxin but specifically reacts with $\beta$-G to express an enzymatic activity (or to induce to express enzymatic activity) and another substance(s) which does not react with endotoxin but specifically reacts with PG to express an enzymatic activity (or to induce to express enzymatic activity). When the substance(s) which reacts with $\beta$-G to express the enzymatic activity (or to induce to express enzymatic activity) is removed, there can be obtained the fraction which specifically reacts with PG. In contrast, when the substance(s) which reacts with PG to express the enzymatic activity (or to induce to express enzymatic activity) is removed, there can be obtained the fraction which specifically react with $\beta$-G.

As the method for removing substance(s) which reacts with $\beta$-G or PG to express the enzymatic activity (or to induce to express enzymatic activity), there can be used any separation and purification methods conventionally used in the field of biochemistry such as gel filtration, electrophoresis, high performance liquid chromatography, affinity chromatography, etc. Among these methods, affinity chromatography using a carrier bonded to $\beta$-G or PG is particularly preferable due to its remarkably easy and effective operation.

Such affinity chromatography is explained below in detail.

As the carrier for bonding $\beta$-G or PG, there can be used cellulose, agarose, dextran, polyacrylamide, porous glass, etc. These carriers are usually used as carriers in the affinity chromatography. Among them, agarose is particularly preferable. Commercially available carriers are agarose type carriers such as Sepharose (Pharmacia Fine Chemicals), Biogel A (Bio-Rad Laboratories); dextran type carriers such as Sephadex (Pharmacia Fine Chemicals), P-L DEX (P-L Biochemicals); polyacrylamide type carriers such as Sephacryl (Pharmacia Fine Chemicals), Biogel P (Bio-Rad Laboratories), etc.

In order to bond $\beta$-G or PG to such a carrier, it is necessary to activate the carrier. The carrier can be activated, for example, by activation with CNBr in the case of bonding PG to an agarose type carrier. It is also possible to use epoxy activated (epichlorohydrin activated) agarose as activated agarose for both β-G and PG.

As the β-G bonded to a carrier, there can be used natural one obtained from various bacteria (e.g. *Alcaligenes genus, Laminaria genus, Agrobacterium genus*, etc.), yeasts (e.g. *Saccharomyces genus*, etc.), and mushrooms (e.g. *Cortinellus shiitake, Schizophyrum commune, Coriolus versicolor*); or storage polysaccharide of algae, e.g. brown algae, Euglena, diatomeae, etc.

In the case of using a material such as curdlan which can be processed to an insoluble carrier (e.g. beads) by itself in place of using the carrier bonded to β-G mentioned above, it is possible to use such a material as a carrier without bonding to other carrier to carry out the affinity chromatography. The curdlan beads used for such a purpose can be prepared, for example, by processes disclosed in U.S. Pat. Nos. 4,143,201 and 4,493,894.

On the other hand, as the PG bonded to a carrier, there can be used natural one obtained from cell walls of various bacteria (e.g. *Micrococcus genus, Streptococcus genus, Mycobacterium genus, Bacillus genus, Staphylococcus genus*, etc); or a decomposed (digested) PG which is decomposed (digested) to some extent by a suitable enzyme such as egg white lysozyme and the like. It is also possible to use PG itself as a carrier in place of the carrier bonded to PG for carrying out affinity chromatography.

In order to carry out affinity chromatography more effectively, it is desirable to remove previously the influence of cations such as $Ca^{2+}$, $Mg^{2+}$, etc., present in the body fluid by adding a chelating agent or the like to plasma and eluate for affinity chromatography. As the chelating agent, there can be used sodium ethylenediaminetetraacetate (EDTA), ethylene glycol bis(β-aminoethyl ether)-N,N,N',N'-tetraacetate sodium salt (EGTA), and the like. The chelating agent is preferably used in a concentration of 1 to 10 mM in plasma or eluate. It is also possible to use the above-mentioned SPI in place of the chelating agent. Preferable amount of SPI in plasma or eluate is 0.1 to 10 mM, more preferably 0.5 to 5 mM.

The procedure of affinity chromatography can be carried out according to the conventional procedure.

By treating the insect plasma by the affinity chromatography using the carrier bonded to β-G or PG mentioned above, the fraction which specifically reacts with PG or β-G can easily be obtained.

By using the thus obtained fraction, the determination of β-G or PG can be carried out as follows.

A sample containing β-G or PG is well mixed with a reagent comprising a fraction which specifically reacts with β-G or PG (hereinafter referred to as "β-G reagent" or "PG reagent") to prepare a reaction solution. After a certain period of time, an enzymatic activity, e.g. activity of BAEEase, PPAE, PO, etc., in the reaction solution is measured by a conventional method and compared with calibration curves previously obtained by using β-G or PG standard solutions with known concentrations to determine the amount of β-G or PG (hereinafter this method is referred to as "end method").

Alternatively, it is possible to apply a phenomenon that a time required for the activation of PO depends on the concentration of β-G or PG in the sample. That is, after mixing the β-G reagent or PG reagent with a sample in the presence of the substrate of PO, a time required for reaching a certain value of the amount of reaction product generated by PO is measured. This method was devised by the present inventors (hereinafter referred to as "time method").

Prior to the determination of β-G or PG by using either the end method or the time method, it is necessary to add divalent metal ions such as $Ca^{2+}$, $Mg^{2+}$, or the like, which are removed from the reagent solution during the preparation of the fraction which specifically reacts with β-G or PG, to the reaction solution. Final concentration of these divalent metal ions in the reaction solution is preferably about 4 to 10 mM.

In this invention, it is possible to use additives or reagents which are necessary for conventional determination of enzymatic activities, for example, substrates, buffers, coupling enzymes, coenzymes, as well as color developing agents, enzyme activity imparting agents, stabilizers for enzymes and dyes, surface active agents, etc., depending on enzymes of which activities to be measured. These additives or reagents may be dissolved in the β-G or PG reagent previously, or in the case of end method, it is possible to react a part of the reaction solution not containing these additives or reagents which is taken out as a sample with a reagent for measuring enzymatic activity.

In the determination of β-G or PG by using these methods, the reaction temperature is not particularly limited so long as the reaction between a sample containing β-G or PG and the β-G or PG reagent can proceed, and is preferably 20° to 40° C.

The reaction pH changes depending on enzymes to be measured. In order to maintain the reaction pH, a buffer is usually used so long as it does not influence the reaction. Examples of the buffers are phosphate buffer, borate buffer, acetate buffer, Tris-HCl buffer, Good's buffer, etc.

As β-G measurable by the methods mentioned above, there are so-called β-G such as zymosan, curdlan, pachyman, etc.; glucose polymers having β-1,3-linkage and derivatives thereof such as Sclerotan, lentinan, schizophyllan, coriolan, laminaran, lichenan, etc.

This invention is illustrated by way of the following Examples, but not limited thereto.

REFERENCE EXAMPLE 1

Preparation of Silkworm Plasma

Silkworm plasma was prepared according to the Ashida method (Insect Biochem., 11, 57–65, 1981) as follows.

Silkworm larvae of fifth instar were anesthetized on ice for 10 min. An amount of half the body weight of physiological saline containing 20 mM of cane sugar or 6 μg/ml of cane sugar factor purified from sugar cane was injected into haemocoel through a hypodermic needle inserted at the junction of the fifth and sixth abdominal segments. After the injection, the larvae body was tied with a fine thread at the posterior part of the fifth abdominal segment to prevent leakage of the injected saline. After allowing to stand at room temperature for 20 minutes, a leg was cut for bleeding at the third abdominal segment. The collected hemolymph was centrifuged at 1500 g for 5 minutes at a low temperature (about 4° C.) to remove hemocytes. The supernatant in an amount of about 100 ml was subjected to dialysis at a low temperature for 2 days against 3 liters of 0.01 M-tris-malate buffer (pH 6.5 containing 0.15 M KCl) to give the desired silkworm plasma.

REFERENCE EXAMPLE 2

Preparation of Peptidoglycan

Cell walls of Micrococcus luteus ATCC 4698 was suspended in 150 ml of cold water and 0.6 g/ml of glass beads of 0.1 mm in diameter were added thereto. Ultrasonic treatment was carried out at 0° C. to break the cell walls. After removing the glass beads, centrifugation was conducted at 2200 g for 10 minutes to remove a precipitation, followed by centrifugation of the supernatant at 20000 g for 45 minutes. The obtained precipitate was suspended in 150 ml of a 1 M NaCl solution, followed by collection of fractions by centrifugation at 2200 g to 20000 g to give a crude cell wall preparation.

The obtained crude cell wall preparation was suspended in 80 ml of water, heated at 100° C. for 20 minutes, cooled, added with 140 ml of 2M acetic acid-sodium acetate buffer (pH 5.9) and 10 mg of ribonuclease and incubated at 37° C. for 3 hours. Then, centrifugation was conducted at 20000 g for 1 hour and the obtained precipitate was suspended in a 50 mM Tris-HCl buffer [pH 7.5, containing 20 mM MgCl$_2$, mM CaCl$_2$ and 7 mg of DNase I (mfd. by Sigma Chem. Co., Ltd.) and incubated at 37° C. for 3 hours. Subsequently, centrifugation was conducted at 20000 g for 1 hour, and the obtained precipitate was suspended in 100 ml of a 0.4% sodium dodecylsulfate solution and allowed to stand at room temperature for 1 hour. Then the precipitate was washed with distilled water 6 times, followed by freeze-drying to give a purified cell wall preparation.

The obtained pure cell wall preparation was suspended in 0.1N HCl and allowed to stand at 60° C. for 24 hours. Then, centrifugation was conducted at 20000 g for 1 hour, and the obtained precipitate was washed with distilled water and freeze-dried to give peptidoglycan.

REFERENCE EXAMPLE 3

Preparation of Curdlan Beads Column

To 9 g of curdlan powder (mfd. by Wako Pure Chemical Industries, Ltd.), 270 ml of pure water was added and stirred to give a slurry. When 30 ml of 1N NaOH was add to the slurry, the curdlan was dissolved to give a sodium hydroxide aqueous solution of curdlan. In a 8-liter beaker, 1200 ml of toluene and 6 g of surface active agent Emalex HC-80 (a trade name, polyoxyethylene cured castor oil derivative, mfd. by Nihon Emulsion Co., Ltd.) were placed and added thereto dropwise the sodium hydroxide aqueous solution of curdlan at room temperature with stirring at a speed of 800 r.p.m. using a screw-type stirrer. The thus obtained curdlan dispersion was added to a liquid comprising 2000 ml of toluene and 1000 ml of acetic acid with stirring at a rate of 800 r.p.m. After stirring for 1 hour, the resulting curdlan dispersion was allowed to stand about 8 hours to precipitate produced beads. The solvent was removed by decantation. The obtained precipitate was washed with 8 liters of pure water 5 times to make the pH neutral, to remove the organic solvent completely to give 240 ml of curdlan beads.

The beads were classified and those of particle size of 50 to 100 μm (average particle size: about 80 μm) were equilibrated with 0.01 M tris-malate buffer (pH 6.5, containing 0.15 M KCl and 1 mM EDTA; hereinafter referred to as "TMB") and packed in a column (1.3 cm in diameter and 2.3 cm long) to give a curdlan beads column.

EXAMPLE 1

Silkworm larvae (Bombyx mori) of fifth instar were anesthetized on ice for 10 min. A leg was cut at the third abdominal segment and hemolymph leaked out was dropped into 10 ml of a 0.9% NaCl solution containing 2 mM of p-APMSF and collected. About 15 ml of hemolymph was obtained from 25 silkworm larvae. From this, about 25 ml of a hemolymph diluted solution was obtained. The hemolymph diluted solution was centrifuged at 1500 g for 5 minutes to remove hemocytes. To 25 ml of the resulting supernatant, 37.5 ml of saturated ammonium sulfate solution was added to give a 60% saturated ammonium sulfate suspension, which was centrifuged at 10000 g for 20 minutes to give a precipitate. This precipitate was dissolved in 27 ml of 0.01 M Tris-malate buffer (pH 6.5, containing 0.15 M NaCl), added with 0.1 ml of a 200 mM p-APMSF solution and dialyzed 4 times against 1 liter of 0.01 M Tris-malate buffer (pH 6.5, containing 0.15 M NaCl). The dialyzed solution was centrifuged at 10000 g for 20 minutes at low temperatures to give the desired silkworm plasma.

The same results were also obtained when NPGB was used in place of p-APMSF.

EXAMPLE 2

Silkworm larvae (Bombyx mori) of fifth instar were anesthetized on ice for 10 minutes. A 0.9% NaCl solution containing 2 mM of p-APMSF was injected into haemocoel at the junction of the fifth and sixth abdominal segments. After the injection, the larvae body was tied with a fine thread at the posterior part of the fifth abdominal segment to prevent leakage of the injected saline. Then, a leg was cut at the third abdominal segment to collect a body fluid (hemolymph) leaked out. The collected hemolymph was centrifuged at 1500 g for 5 minutes at low temperatures to remove hemocytes. To 10 ml of the obtained supernatant, 0.05 ml of a 200 mM p-APMSF solution was added and centrifuged at 10000 g for 20 minutes at low temperatures. The supernatant was passed through a Sephadex G-25 column (2.5 cm in diameter and 25 cm long) equilibrated with 0.01 M Tris-malate buffer (pH 6.5, containing 0.15 M NaCl). After collecting peaks of protein eluted into void volume of the column, the desired silkworm plasma was obtained.

EXAMPLE 3

(1) Preparation of Sepharose 4B Column Coupled with Peptidoglycan

The purified peptidoglycan obtained in Reference Example 2 in an amount of 153 mg was suspended in 153 ml of 80 mM ammonium acetate and 1.5 mg of egg white lysozyme was added thereto. After heating at 45° C. for 4 minutes with stirring, digestion was carried out at 37° C. for 2 hours. Then, the reaction solution was filtered with a millipore filter (HAWPO 4700) and the filtrate was freeze-dried. The freeze-dried product was dissolved in 6 ml of distilled water. The resulting solution in an amount of 5.5 ml was subjected to gel filtration using a Sephadex G-50 SF column (eluate: a 50 mM ammonium carbonate solution; column 2.5 cm in diameter and 90 cm long; elution rate; 15 ml/hr). Central portions of active fractions of reducing sugar produced by the digestion were collected and freeze-dried. The freeze-dried product was dissolved in 6.3 ml of 0.1 M sodium carbonate buffer (pH 10) to give a peptidoglycan solution. The peptidoglycan solution was reacted with 2.7 g of CNBr activated Sepharose 4B (mfd. by Pharmacia Fine Chemicals) according to a conventional method to give Sepharose 4B coupled with peptidoglycan.

The thus obtained Sepharose 4B coupled with peptidoglycan was packed in a column (0.6 cm in diameter and 1.7 cm long) and equilibrated with TMB to give a PG column. (2) Preparation of β-G Reagent.

To the silkworm plasma obtained in Reference Example 1, a 100 mM EDTA solution (pH 6.5) was added so as to make the final concentration of EDTA 1 mM. 15 Ml of the resulting solution was treated with the PG column obtained in above (1) (eluate: TMB; elution rate: 6 ml/hr). The eluate in an amount of 12 ml obtained immediately after pouring the sample was collected to give a β-G reagent.

(3) Measurement of Activation of Zymogens (inactive forms of BAEEase, PPAE and PO) by Zymosan (β-1,3-glucan) or PG in β-G Reagent or Silkworm Plasma. [Measuring procedure]

To 200 μl of the silkworm plasma obtained in Reference Example 1 or the β-G reagent obtained in (2), 0 20 μl of a 80 mM CaCl$_2$ solution was added and further 1 mg/ml of Zymosan solution or 1 mg/ml of PG solution was added thereto with well mixing to react at 25° C. The reaction solution was sampled at intervals to measure the degree of activation of PO or BAEEase activity value.

① Measurement of PO Activity

To 1 ml of a substrate solution (a 0.1 M phosphate buffer containing 4 mM 4-methylcatechol and 8 mM 4-hydroxyproline ethyl ester, pH 6.0), 10 μl of a sample (the above-mentioned reaction solution) was added and reacted at 30° C. for 10 minutes. Then, absorbance of the produced quinone dye stuff at 520 nm was measured to obtain the degree of activity of PO.

Figure 1:
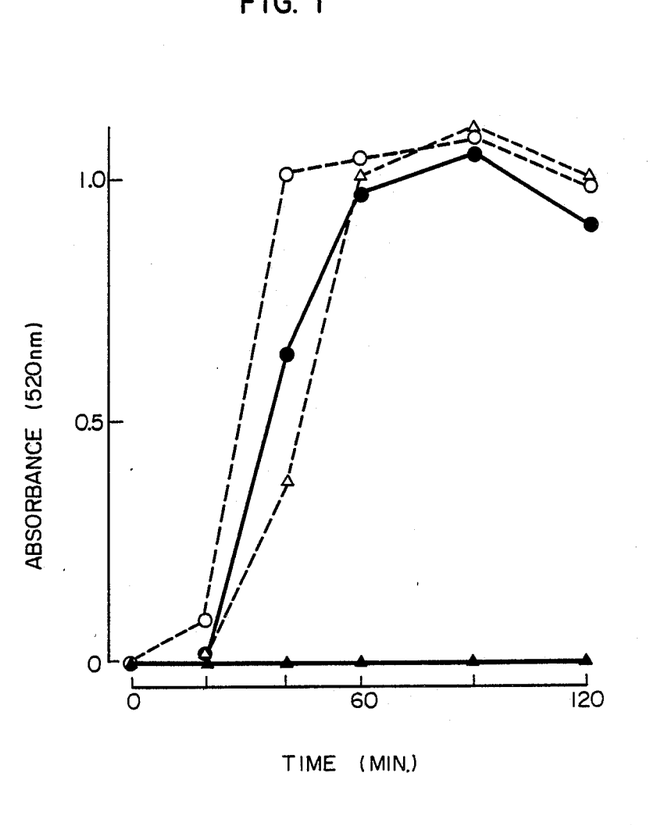
FIG. 1 is a graph showing a change of absorbance at 520 nm depending on reaction time when various samples obtained in Example 3 are reacted with substrate solutions.

FIG. 1 shows changes of absorbance at 520 nm depending on the reaction time when various samples were reacted with the substrate solution. In FIG. 1, the changes of absorbance are shown by the curve—●—in the case of reacting zymosan with the β-G reagent,—▲—in in the case of reacting PG with the β-G reagent,—○—in the case of reacting zymosan with the silkworm plasma, and—△—in the case of reacting PG with the silkworm plasma.

② Measurement of BAEEase Activity

To 1 ml of a substrate solution [containing o 2 mM N-α-benzoyl-L-arginine ethyl ester, 1 mM AND (nicotinamide adenine dinucleotide), 0.1 mg/ml alcohol dehydrogenase, 0.25 M tris(hydroxymethyl)aminomethane, and 0.2 M semicarbazide, pH 8.5]previously heated at 25° C., 30 μl of a sample (the above-mentioned reaction solution) was added and well mixed to react at 25° C. An increase of absorbances at 340 nm of NADH (nicotinamide adenine dinucleotide, reduced form) produced by the reaction was measured. One unit (U) of BAEEase is defined as an amount which can produce 1 nmole of ethanol in one minute under the above-mentioned conditions.

The results are shown in Table 1.

TABLE 1

| Reagent | Sample solution | BAEEase activity (U/ml) |
|---|---|---|
| Silkworm plasma | Zymosan solution | 93.7 |
| | PG solution | 91.0 |
| β-G | Zymosan solution | 84.0 |

TABLE 1-continued

| Reagent | Sample solution | BAEEase activity (U/ml) |
|---|---|---|
| reagent | PG solution | 0.0 |

As is clear from Table 1, the enzymes in the silkworm plasma are activated by zymosan and PG, but the enzymes in the β-G reagent are only activated by zymosan and not activated by PG.

The same results as mentioned above were obtained when the β-G reagents prepared by using the silkworm plasma obtained in Examples 1 and 2 were used.

EXAMPLE 4

Formation of Calibration Curve for β-1,3-glucan using Curdlan

[Measuring procedure]

To 2 ml of the β-G reagent obtained in Example 3(2), 200 μl of a 80 mM CaCl$_2$ solution was added and mixed well. To 10 μl of the resulting mixture, 10 μl of a curdlan solution with a predetermined concentration was added and incubated at 30° C. for 60 minutes. Then, 1 ml of the same substrate solution for measuring PO activity as used in Example 3(3) was added and reacted at 30° C. for 10 minutes, followed by measurement of absorbance at 520 nm (measured value: Es). Blank value ($E_{Bl}$) was obtained in the same manner as mentioned above by using purified water in place of the curdlan solution.

[Results]

Figure 2:
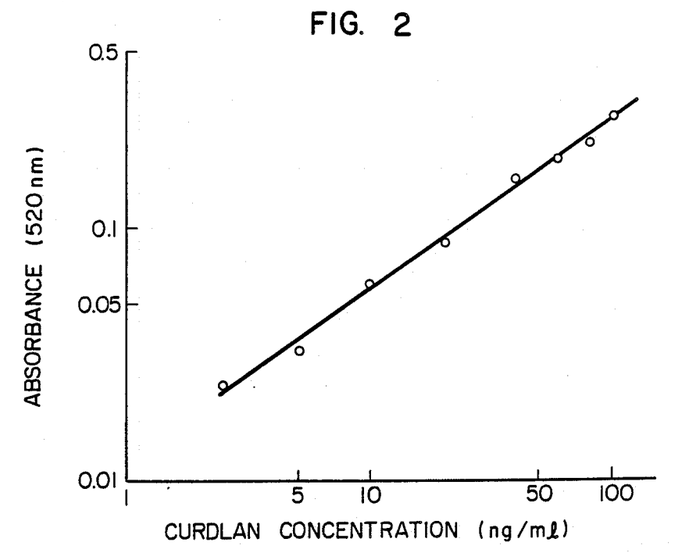
FIG. 2 shows a calibration curve obtained in Example 4.

FIG. 2 shows the relationship between the curdlan concentration and ($E_S - E_{Bl}$) values by using logarithmic scales at both ordinate and abscissa axes.

As is clear from FIG. 2, good linearity is obtained.

EXAMPLE 5

Formation of Calibration Curve for β-1,3-glucan using Curdlan

[Measuring procedure]

To 2 ml of the β-G reagent obtained in Example 3(2), 200 μl of a 80 mM CaCl$_2$ solution was added and mixed well. To 70 μl of the resulting mixture, 70 μl of 0.1 M phosphate buffer (containing 20 mM L-dopa, pH 6.0) and 70 μl of a curdlan solution with a predetermined concentration were added and mixed well. Then, by using a Toxinometer ET-201 (mfd. by Wako Pure Chemical Industries, Ltd.), a time (Δt) required for reducing the transmitted light amount by 5% at 30° C. was measured.

[Results]

Figure 3:
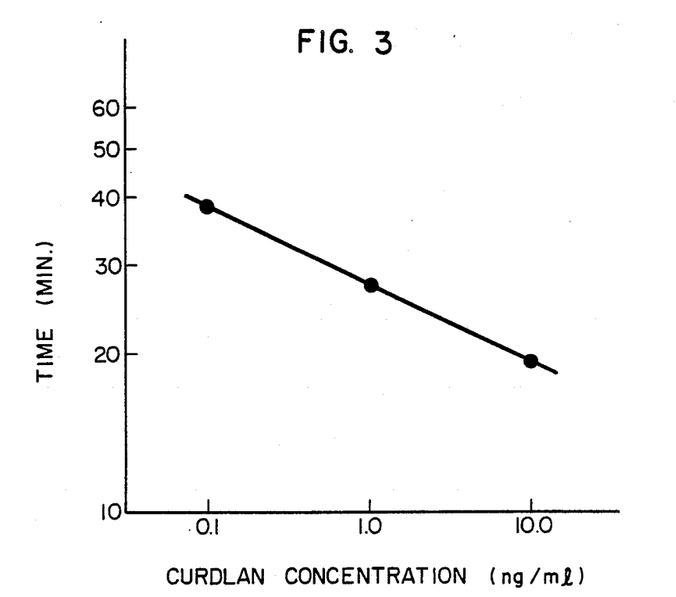
FIG. 3 shows a calibration curve obtained in Example 5.

FIG. 3 shows the relationship between the Δt and the curdlan concentration by using logarithmic scales at both ordinate and abscissa axes.

As is clear from FIG. 3, good linearity is obtained.

As mentioned above, by using the reagent containing the component which specifically reacts with β-G, β-G can be determined. By using such a determination process, the detection of contamination with true fungi, examinations of blood dialysis films of cellulose derivatives, examinations of reactive substances reactive to Limulus test other than endotoxin, etc., can be carried out with easy and precisely.

EXAMPLE 6

(1) Preparation of PG Reagent

To 5 ml of the silkworm plasma obtained in Reference Example 1, 20 ml of TMB was added and mixed well to give a sample, which was treated with the curdlan beans column obtained in Reference Example 3. The protein fraction passed through in an amount of about 25 ml was dropped in 225 ml of a saturated ammonium sulfate solution, followed by stirring overnight. A precipitate was collected by centrifugation (at 16000 g for 20 minutes) and then dissolved in 4 ml of TMB, followed by dialysis against 500 ml of TMB. The resulting solution was centrifuged again (at 16000 g for 20 minutes) and the supernatant was made 5 ml as a total with TMB to give a PG reagent.

(2) Measurement of Activation of Zymogens (inactive forms of BAEEase, PPAE and PO) by Zymosan ($\beta$-1,3-glucan) or PG in PG Reagent or Silkworm Plasma.

[Measuring procedure]

To 200 $\mu$l of the silkworm plasma obtained in Reference Example 1 or the PG reagent obtained in above (1), 20 $\mu$l of a 80 mM CaCl$_2$ solution was added and further 20 $\mu$l of a 1 mg/ml zymosan solution or a 1 mg/ml PG solution (prepared by using that obtained in Reference Example 2) was added and mixed well to react at 25° C. The reaction solution was sampled at intervals to measure the degree of activation of PO or BAEEase activity value.

① Measurement of PO Activity

To 1 ml of a substrate solution (a 0.1 M phosphate buffer containing 4 mM 4-methylcatechol and 8 mM 4-hydroxyproline ethyl ester, pH 6.0), 10 $\mu$l of a sample (the above-mentioned reaction solution) was added and reacted at 30° C. for 10 minutes. Then, absorbance of the produced quinone dye stuff at 520 nm was measured to obtain the degree of activity of PO.

Figure 4:
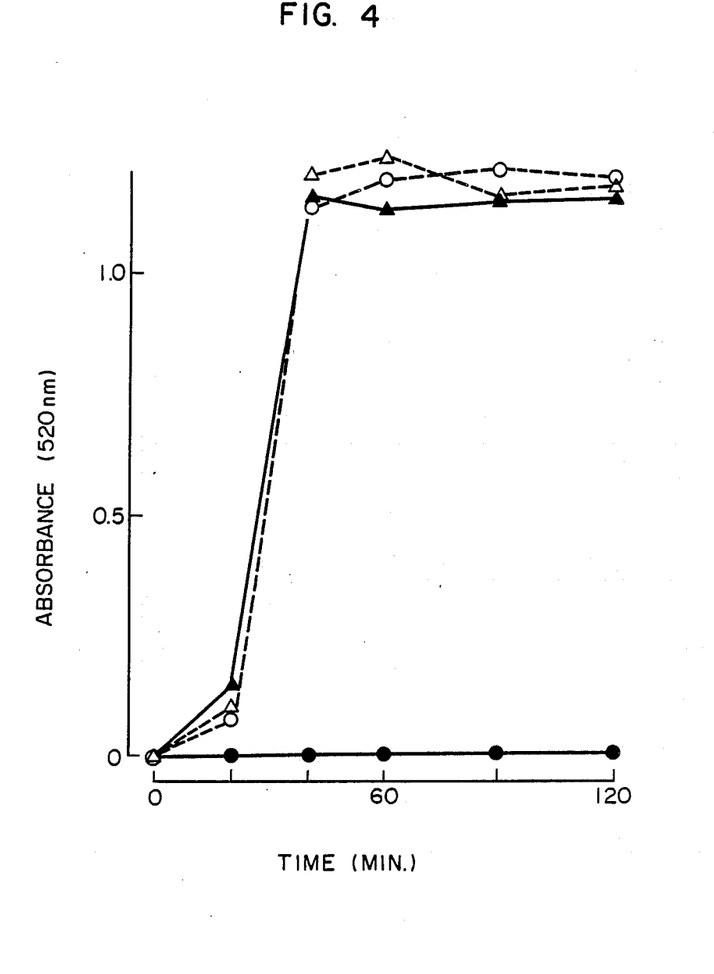
FIG. 4 is a graph showing a change of absorbance at 520 nm depending on reaction time when various samples obtained in Example 6 are reacted with substrate solutions.

FIG. 4 shows changes of absorbance at 520 nm depending on the reaction time when various samples were reacted with the substrate solution. In FIG. 4, the changes of absorbance are shown by the curve— ●—in the case of reacting zymosan with the PG reagent,—▲—in in the case of reacting PG with the PG reagent,— ○—in in the case of reacting zymosan with the silkworm plasma, and —△—in the case of reacting PG with the silkworm plasma.

② Measurement of BAEEase Activity.

To 1 ml of a substrate solution [containing 2 mM N-$\alpha$-benzoyl-L-arginine ethyl ester, 1 mM NAD (nicotinamide adenine dinucleotide), 0.1 mg/ml alcohol dehydrogenase, 0.25 M tris(hydroxymethyl)aminomethane and 0.2 M semicarbazide, pH 8.5]previously heated at 25° C., 30 $\mu$l of a sample (the above-mentioned reaction solution) was added and well mixed to react at 25° C. An increase of absorbances at 340 nm of NADH (nicotinamide adenine dinucleotide, reduced form) produced by the reaction was measured. One unit (U) of BAEEase is defined as an amount which can produce 1 nmole of ethanol in one minute under the above-mentioned conditions.

The results are shown in Table 2.

TABLE 2

| Reagent | Sample solution | BAEEase activity (U/ml) |
|---------|-----------------|-------------------------|
| Silkworm plasma | Zymosan solution | 93.7 |
| | PG solution | 91.0 |
| PG reagent | Zymosan solution | 0.0 |
| | PG solution | 89.3 |

As is clear from Table 2, the enzymes in the silkworm plasma are activated by zymosan and PG, but the enzymes in the PG reagent are only activated by PG and not activated by zymosan.

The same results as mentioned above were obtained when the PG reagents prepared by using the silkworm plasma obtained in Examples 1 and 2 were used.

EXAMPLE 7

Formation of Calibration Curve for PG

[Measuring procedure]

To 2 ml of the PG reagent obtained in Example 6(1), 200 $\mu$l of a 80 mM CaCl$_2$ solution and mixed well. To 10 $\mu$l of the resulting mixture, 10 $\mu$l of the PG solution having a predetermined concentration was added and incubated at 30° C. for 60 minutes. Then, 1 ml of the same substrate solution for measuring PO activity as used in Example 6(2) was added thereto and further reacted at 30° C. for 10 minutes, followed by measurement of absorbance at 520 nm (measured value: $E_S$). Blank value ($E_{Bl}$) was obtained in the same manner as mentioned above by using purified water in place of the PG solution.

[Results]

Figure 5:
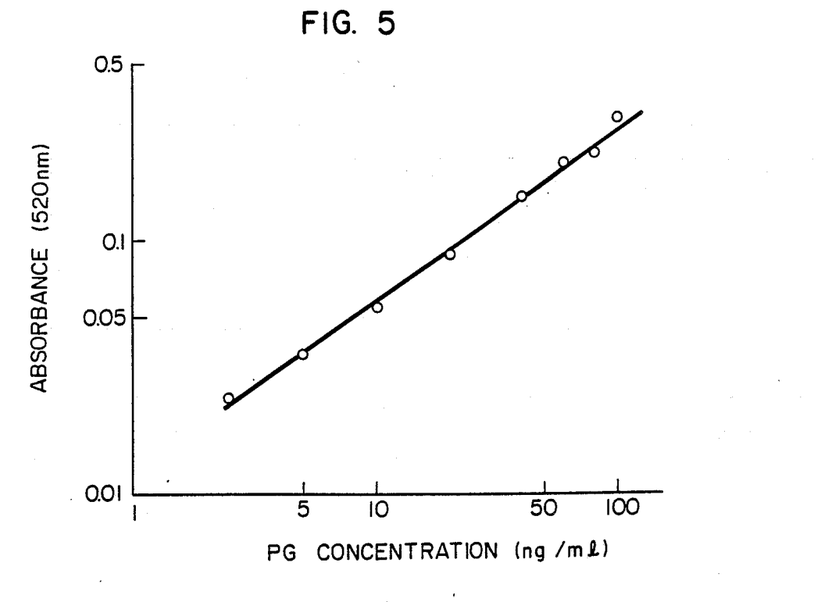
FIG. 5 shows a calibration curve obtained in Example 7.

FIG. 5 shows the relationship between the PG concentration and ($E_S - E_{Bl}$) values by using logarithmic scales at both ordinate and abscissa axes.

As is clear from FIG. 5, good linearity is obtained.

EXAMPLE 8

Formation of Calibration Curve for PG

[Measuring procedure]

To 2 ml of the PG reagent obtained in Example 6(1), 200 $\mu$l of a 80 mM CaCl$_2$ solution was added and mixed well. To 70 $\mu$l of the resulting mixture, 70 $\mu$l of 0.1 M phosphate buffer (containing 20 mM L-dopa, pH 6.0) and 70 $\mu$l of PG solution with a predetermined concentration were added and mixed well. Then, by using Toxinometer ET-201 (mfd. by Wako Pure Chemical Industries, Ltd.), a time ($\Delta$t) required for reducing the transmitted light amount by 5% at 30° C. was measured.

[Results]

Figure 6:
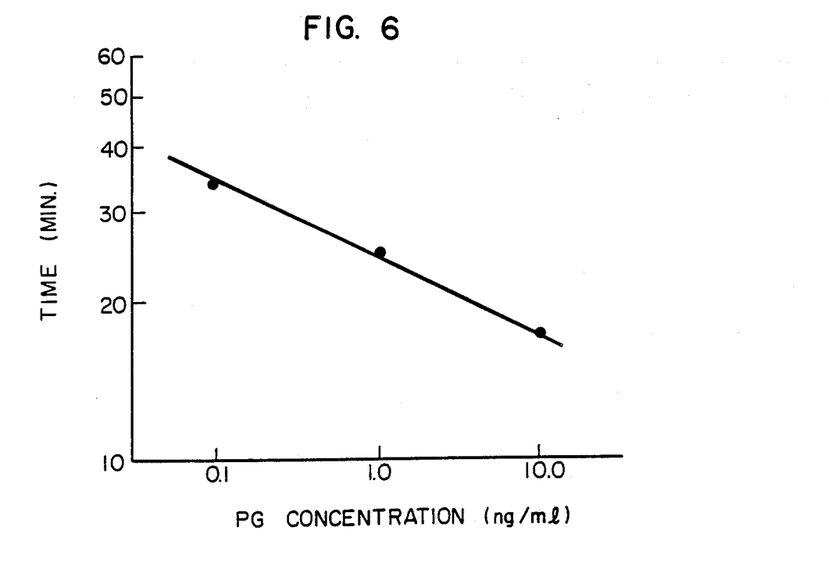
FIG. 6 shows a calibration curve obtained in Example 8.

FIG. 6 shows the relationship between the $\Delta$t and the PG concentration by using logarithmic scales at both ordinate and abscissa axes.

As is clear from FIG. 6, good linearity is obtained.

As mentioned above, by using the reagent containing the component which specifically reacts with PG, PG can be determined. By using such a determination process, PG can be determined easily and precisely.

What is claimed is:

1. A partially purified reagent for determining $\beta$-1,3-glucan comprising a fraction prepared by the process of treating plasma of an insect with a method selected from the group consisting of gel filtration, electrophoresis, high performance liquid chromatography and affinity chromatography, wherein a substance which reacts with peptidoglycan is removed from said plasma, and said fraction is capable of reacting specifically with $\beta$-1,3-glucan in the presence of a zymogen of an esterase hydrolyzing N-$\alpha$-benzoyl-L-arginine ethyl ester, prophenoloxidase activating enzyme or phenoloxidase to activate said zymogen.

2. A reagent according to claim 1, wherein said insect is selected from the group consisting of orders Lepidoptera, Diptera, Orthoptera and Coleoptera.

3. A reagent according to claim 1, wherein the insect is silkworm larvae.

4. A reagent according to claim 1, wherein said fraction is prepared by removing said substance which reacts with peptidoglycan from said plasma by affinity chromatography using a carrier bonded to peptidoglycan, said fraction being capable of reacting specifically with β-1,3-glucan.

5. A partially purified reagent for determining peptidoglycan comprising a fraction prepared by the process of treating insect plasma with a method selected from the group consisting of gel filtration, electrophoresis, high performance liquid chromatography and affinity chromatography, wherein a substance which reacts with β1,3-glucan is removed from said plasma, and said fraction is capable of reacting specifically with peptidoglycan in the presence of a zymogen of an esterase hydrolyzing N-α-benzoyl-L-arginine ethyl ester, prophenoloxidase activating enzyme or phenoloxidase to activate said zymogen.

6. A reagent according to claim 5, wherein said insect is selected from the group consisting of orders Lepidoptera, Diptera, Orthoptera and Coleoptera.

7. A reagent according to claim 5, wherein the insect is silkworm larvae.

8. A reagent according to claim 5, wherein said fraction is prepared by removing said substance which reacts with β-1,3-glucan from said plasma by affinity chromatography using a carrier bonded to β-1,3-glucan or β-1,3-glucan alone, said fraction being capable of reacting specifically with peptidoglycan.

9. A process for specifically determining β-1,3-glucan in a sample which comprises:
  combining the reagent of claim 1 with a sample suspected of containing β-1,3-glucan to obtain a mixture;
  incubating the resulting mixture for a pre-determined period of time;
  measuring the enzymatic activity of an esterase hydrolyzing N-α-benzoyl-L-arginine ethyl ester, prophenoloxidase activating enzyme or phenoloxidase; and
  determining β-1,3-glucan from said enzymatic activity.

10. A process for specifically determining β1,3-glucan in a sample which comprises:
  combining the reagent of claim 1 with a sample suspected of containing β-1,3-glucan to obtain a mixture;
  incubating the resulting mixture;
  measuring the time required for activation of a zymogen of an esterase hydrolyzing N-α-benzoyl-L-arginine ethyl ester, prophenoloxidase activating enzyme or phenoloxidase; and
  determining β-1,3-glucan from said time required for activation of said zymogen.

11. A process for specifically determining peptidoglycan in a sample which comprises:
  combining the reagent of claim 5 with a sample of suspected of containing peptidoglycan to obtain a mixture;
  incubating the resulting mixture for a pre-determined period of time;
  measuring the enzymatic activity of an esterase hydrolyzing N-α-benzoyl-L-arginine ethyl ester, prophenoloxidase activating enzyme or phenoloxidase; and determining peptidoglycan from said enzymatic activity.

12. A process for specifically determining peptidoglycan in a sample which comprises:
  combining the reagent of claim 5 with a sample suspected of containing peptidoglycan to obtain a mixture;
  incubating the resulting mixture;
  measuring the time required for activation of a zymogen of an esterase hydrolyzing N-α-benzoyl-L-arginine ethyl ester, prophenoloxidase activating enzyme or phenoloxidase; and
  determining peptidoglycan from said time required for activation of said zymogen.

* * * * *